United States Patent [19]

Henrick

[11] 4,447,613

[45] May 8, 1984

[54] PYRIDYL ESTERS AND THIOLESTERS OF AMINOALKANOIC ACIDS

[75] Inventor: Clive A. Henrick, Palo Alto, Calif.

[73] Assignee: Zoecon Corporation, Palo Alto, Calif.

[21] Appl. No.: 355,792

[22] Filed: Mar. 8, 1982

Related U.S. Application Data

[60] Continuation of Ser. No. 220,335, Dec. 29, 1980, abandoned, which is a division of Ser. No. 158,834, Jun. 12, 1980, Pat. No. 4,269,981, which is a division of Ser. No. 78,525, Sep. 24, 1979, Pat. No. 4,247,701, which is a continuation-in-part of Ser. No. 69,445, Aug. 24, 1979, Pat. No. 4,226,872, which is a continuation-in-part of Ser. No. 16,775, Mar. 2, 1979, abandoned.

[51] Int. Cl.$^3$ .......................................... C07D 213/64
[52] U.S. Cl. .................................. 546/300; 546/298; 546/301; 546/314; 546/330; 546/331; 546/335
[58] Field of Search ............... 546/300, 314, 330, 331, 546/298, 335, 301

[56] References Cited

U.S. PATENT DOCUMENTS

| | | | |
|---|---|---|---|
| 4,223,033 | 9/1980 | Henrick | 424/263 |
| 4,226,872 | 10/1980 | Henrick | 424/263 |
| 4,238,614 | 12/1980 | Henrick | 546/301 |
| 4,247,701 | 1/1981 | Henrick | 546/300 |
| 4,248,875 | 2/1981 | Henrick | 424/263 |
| 4,269,981 | 5/1981 | Henrick | 546/291 |

*Primary Examiner*—Alan L. Rotman
*Attorney, Agent, or Firm*—Jacqueline S. Larson; Donald W. Erickson

[57] ABSTRACT

Pyridyl esters and thiolesters of amino acids, intermediates therefor, synthesis thereof and the use of said esters and thiolesters and compositions for the control of pests.

5 Claims, No Drawings

PYRIDYL ESTERS AND THIOLESTERS OF AMINOALKANOIC ACIDS

This is a continuation of Ser. No. 220,335, filed Dec. 29, 1980, abandoned, which is a division of Ser. No. 158,834, filed June 12, 1980, now U.S. Pat. No. 4,269,981, which is a division of Ser. No. 078,525, filed Sept. 24, 1979, now U.S. Pat. No. 4,247,701, which is a continuation-in-part of Ser. No. 069,445, filed Aug. 24, 1979, now U.S. Pat. No. 4,226,872, which is a continuation-in-part of Ser. No. 016,775, filed Mar. 2, 1979, abandoned, the entire disclosures of which are incorporated herein by reference.

This invention relates to novel esters and thiolesters of α-substituted amino acids, novel intermediates therefor, synthesis thereof, and the control of pests.

The esters and thiolesters of the present invention are represented by the following formula (A):

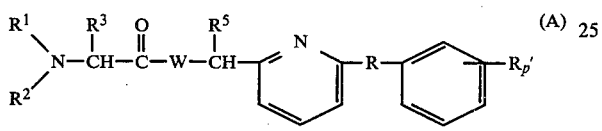

wherein,

W is oxygen or sulfur;
p is zero, one or two;
R is oxygen, sulfur, methylene or carbonyl;
$R^1$ is alkyl, alkenyl, alkynyl, haloalkyl, haloalkenyl, cycloalkyl, cycloalkenyl, alkylthio and haloalkylthio;
$R^2$ is selected from the values of $R^1$ or hydrogen; or $R^1$ and $R^2$ together form a substituted or unsubstituted, saturated or unsaturated ring containing the nitrogen atom;
$R^3$ is lower alkyl of 2 to 5 carbon atoms, lower alkenyl of 2 to 5 carbon atoms or lower cycloalkyl of 3 to 4 carbon atoms;
$R^5$ is hydrogen, cyano, methyl, ethyl, ethynyl, trifluoromethyl or thioamide;
$R'$ is fluoro, bromo, chloro, trifluoromethyl, methyl, methoxy or methylthio; and the salt thereof of a strong organic acid or inorganic acid.

The compounds of the present invention represented by formula (A) are useful agents for the control of pests such as insects and acarids.

In the description hereinafter and the appended claims, each of R through $R^5$, W, and p is as defined hereinabove, unless otherwise specified.

The compounds of formula (A) can be synthesized as outlined below (Y is bromo, chloro or methanesulfonyloxy):

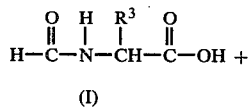

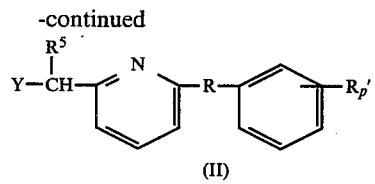

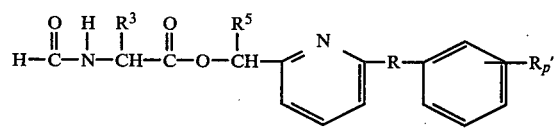

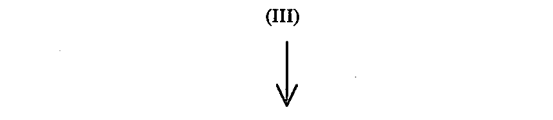

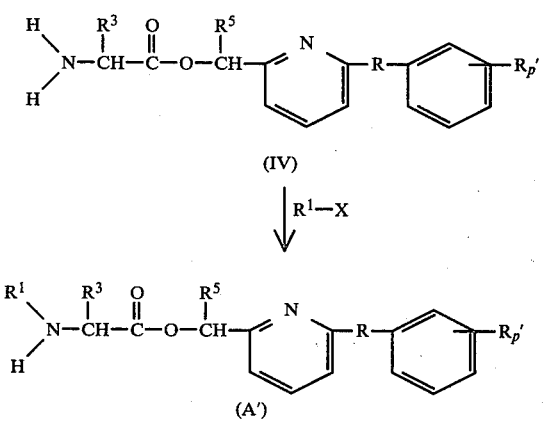

In the general practice of the above synthesis, the acid (I) is reacted with a halide or mesylate of formula II in an organic solvent such as hexamethylphosphoric triamide, tetrahydrofuran or dimethylformamide in the presence of potassium carbonate to form the N-formylamino ester III, which is then hydrogenated to the amino ester IV. This compound is reacted with about one equivalent of the halide $R^1$-X (X is bromo, chloro or iodo) in the presence of a mild base such as diisopropylethylamine in an organic solvent such as the above to obtain the secondary amines of the present invention (A'). The tertiary amines of formula (A) wherein $R^1$ and $R^2$ are the same can be made by using an excess of the halide $R^1$-X. The tertiary amines of formula (A) wherein $R^1$ and $R^2$ are not the same can be made by reacting a secondary amine of formula (A') with the halide $R^2$-X.

In another embodiment, the compounds of formula (A) can be prepared by the reaction of an acid of formula (V) with carbonyl chloride in the presence of an ether such as 1,4-dioxane to form the corresponding oxazolidine-2,5-dione, which is then reacted with an alcohol of formula (VI).

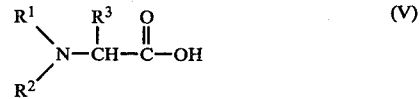

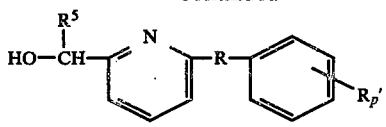

The acids of formula V are prepared by the reaction of an amino acid with a halide $R^1$-X (and/or $R^2$-X) in the presence of a base such as potassium carbonate or diisopropyl ethyl amine. The alcohols of formula VI can be made as described by Malhotra and Ricks, Offenlegungsschrift 28 10 881 and Maeda and Hirose, CA 81 135964k and 80 59873s and references cited therein.

The thiolesters of formula (A) can be prepared by the reaction of the acid of formula I with the S-thiol corresponding to the alcohol of formula VI in the presence of 4-dimethylaminopyridine and dicyclohexylcarbodiimide to give the thiolester corresponding to formula III, which is then hydrogenated and alkylated.

The following terms, wherever used in the description herein and the appended claims, have the meaning defined below, unless otherwise specified hereinafter.

The term "lower alkyl" refers to an alkyl group, straight or branched, having a chain length of one to eight carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkylthio" refers to an alkylthio group, straight or branched, having a chain length of one to eight carbon atoms. The term "lower haloalkylthio" refers to an alkylthio group substituted with one to three halogen atoms.

The term "lower alkenyl" refers to an ethylenically unsaturated hydrocarbon group, straight or branched, having a chain length of two to eight carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms.

The term "lower alkynyl" refers to an alkynyl group, straight or branched, having a chain length of two to eight carbon atoms and one or two acetylenic bonds.

The term "cycloalkyl" refers to a cycloalkyl group of three to eight cyclic carbon atoms.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

Included within the present invention are salts of the compounds of formula A. The salts are formed from strong inorganic acids or organic acids such as hydrochloric acid, sulfuric acid, phosphoric acid, p-toluenesulfonic acid, p-benzenesulfonic acid, methanesulfonic acid, Lewis acid and the like. Many of the compounds of formula A are oils which advantageously are converted into the salt for convenience of handling and formulating and superior stability. The salts are useful for the control of pests in the same way as the compounds of formula A.

The compounds of the present invention of formula A are useful pest control agents, particularly for the control of insects and acarids. In the use of the compounds of formula A for combating insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 percent, by weight.

The compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin and resmethrin.

The following examples are provided to illustrate the practice of the present invention. Temperature is given in degrees Centigrade. RT means room temperature.

EXAMPLE 1

A. To valine (15 g, 0.129 mol) in 88% formic acid (52 ml) is added acetic formic anhydride (33 g, 0.386 mol) over 0.75 hr at 5°. The reaction mixture is warmed to RT and stirred overnight. The reaction is worked up by distilling off (bath temp. 45°–50°) the solvent, excess anhydride and acetic acid, to give, as a white solid, 2-(N-formylamino)-3-methylbutanoic acid, recrystallized from hot ethanol, m.p. 143°–145°.

B. To 6.89 mmol of the product of part A in 10 ml of hexamethylphosphoric triamide (HMPA) is added (6-phenoxy-2-pyridyl)methyl bromide (7.23 mmol) followed by anhydrous potassium carbonate (7.23 mmol). The reaction mixture is stirred, at 24°, for 48 hours and then worked up by pouring into ice-water and extracting with ether (3X). The combined ether extracts are washed with water (2X) and with brine, dried over calcium sulfate and evaporated under vacuum to give (6-phenoxy-2-pyridyl)methyl 2-(N-formylamino)-3-methylbutanoic acid.

C. To the ester (1.6 mmol) of part B, in 2 ml of anhydrous methanol, is added 1 N methanolic HCl (1.8 mmol). The reaction mixture is stirred at RT for 27 hours and then the methanol removed under vacuum. The residue is poured into ice-water followed by removal of neutral impurities with ether. The aqueous layer is made basic by addition of 10% sodium hydroxide and then extracted with ether (3X 30 ml). The combined ether phases are washed with water until neutral and brine and then dried over calcium sulfate, filtered and rotoevaporated to give (6-phenoxy-2-pyridyl)methyl 2-amino-3-methylbutanoate.

EXAMPLE 2

A mixture of (6-phenoxy-2-pyridyl)methyl 2-amino-3-methylbutanoate (3.34 mmol), N,N-diisopropylethylamine (6.68 mmol) and methyl iodide (6.68 mmol) in 5 ml tetrahydrofuran is stirred overnight at RT. It is then worked up by pouring into ice-water (ph $\approx$ 8–9) and extracting with ether. The combined ether layers are washed with water until neutral and with brine, dried over calcium sulfate, and solvent removed, yielding (6-phenoxy-2-pyridyl)methyl 2-(N,N-dimethylamino)-3-methylbutanoate.

EXAMPLE 3

A. Phosgene is bubbled slowly over a period of 3 hr into a stirred suspension of racemic valine (0.26 mole) in 1000 ml of dioxane at RT. The mixture is stirred at RT for 6 hr longer then is stored overnight at −20°. Excess phosgene and most of the solvent are removed by distillation at atmospheric pressure. To the residue is added 0.26 mole of (6-phenoxy-2-pyridyl)methanol along with 500 ml of ether saturated with hydrogen chloride. The resulting mixture is stirred at RT overnight and filtered to remove solid material. The filtrate is stripped of solvent at reduced pressure, then partitioned between ether and saturated aqueous sodium bicarbonate. The organic phase is dried over magnesium sulfate and stripped of solvent. The liquid is treated with an aqueous solution of p-toluenesulfonic acid monohydrate to give the product which is then collected by filtration to give the p-toluenesulfonic acid salt of (6-phenoxy-2-pyridyl)methyl 2-amino-3-methylbutanoate.

B. In 5 ml dimethylformamide is placed 4.6 mmol of 3-chloro-2-buten-1-yl chloride, 3.54 mmol of the p-toluenesulfonic acid salt of (6-phenoxy-2-pyridyl)methyl 2-amino-3-methylbutanoate and 10.6 mmol of N,N-diisopropylethylamine. After stirring at RT for 35 hours, the solution is brought up in ether, washed with water (3X) and with brine, and dried over sodium sulfate to yield a mixture of the cis and trans isomers of (6-phenoxy-2-pyridyl)methyl 2-[N-(3-chloro-2-butenyl)amino]-3-methylbutanoate.

EXAMPLE 4

Following the procedure of Example 2, (6-phenoxy-2-pyridyl)methyl 2-amino-3-methylbutanoate and 2-propyn-1-yl bromide are reacted, resulting in a mixture of two end products, which are separated to give (6-phenoxy-2-pyridyl)methyl 2-[N-(2-propynyl)amino]-3-methylbutanoate and (6-phenoxy-2-pyridyl)methyl 2-[N,N-(di-2-propynyl)amino]-3-methylbutanoate.

In the same manner, (6-phenoxy-2-pyridyl)methyl 2-amino-3-methylbutanoate is reacted with the halide of column I to yield the corresponding N-substituted amino acid ester of column II.

I 1-propyl iodide
3,3-dichloro-2-propen-1-yl bromide
1-methylpropyl bromide
2-chloro-2-propen-1-yl bromide

II (6-phenoxy-2-pyridyl)methyl 2-(N-isopropylamino)-3-methylbutanoate.
(6-phenoxy-2-pyridyl)methyl 2-[N-(3,3-dichloro-2-propenyl)amino]-3-methylbutanoate
(6-phenoxy-2-pyridyl)methyl 2-[N-(1-methylpropyl)amino]-3-methylbutanoate
(6-phenoxy-2-pyridyl)methyl 2-[N-(2-chloro-2-propenyl)amino]-3-methylbutanoate Again following the same procedure, (6-phenoxy-2-pyridyl)methyl 2-(N-isopropyl-N-methylamino)-3-methylbutanoate is prepared from methyl iodide and (6-phenoxy-2-pyridyl)methyl 2-(N-isopropylamino)-3-methylbutanoate.

EXAMPLE 5

Following the method described by Borch et al., *JACS* 93: 2897(1971), the pH of a solution of (6-phenoxy-2-pyridyl)methyl 2-amino-3-methylbutanoate (6.68 mmol) in 30 ml methanol is brought to about pH 6 by addition of concentrated sulfuric acid, after which cyclohexanone (6.1 mmol), 3 A sieves and finally sodium cyanoborohydride (4.0 mmol) are added.

The reaction is stirred at RT for 24 hours, keeping the pH at about 6. The solution is worked up, the methanol is rotoevaporated off, and the residue is poured into water and 10% sodium carbonate. The product is extracted with ether, then filtered and isolated, yielding (6-phenoxy-2-pyridyl)methyl 2-cyclohexylamino-3-methylbutanoate.

EXAMPLE 6

To 10 ml methanol is added 2-bromo-3-methylbutanoic acid (1.39 g, 7.7 mmol) and 1 drop phenolphthalein and the solution is brought to neutral with methanolic sodium hydroxide. The solvent is removed, 4-methyl-1,2,5,6,-tetrahydropyridine (1 g, 10.2 mmol) is added, and the solution is stirred at 95° C. for 2.5 hours, after which it is cooled to RT and washed with ether in 10% sodium hydroxide. The aqueous phase is stripped of water.

The resulting 2-(4-methyl-1,2,5,6-tetrahydro-1-pyridyl)-3-methylbutanoic acid (7.0 mmol) is combined with (6-phenoxy-2-pyridyl)methyl bromide (7.0 mmol) and potassium carbonate (14.0 mmol) in 15 ml dimethylformamide, and the mixture is stirred at RT, under nitrogen, for 20 hours. The solution is brought up in ether, washed with water (3X) and brine, and dried over sodium sulfate to give (6-phenoxy-2-pyridyl)methyl 2-(4-methyl-1,2,5,6-tetrahydro-1-pyridyl)-3-methylbutanoate.

EXAMPLE 7

Following the procedure of Example 1, [6-(4-fluorophenoxy)-2-pyridyl]methyl bromide can be reacted with 2-(N-formylamino)-3-methyl-butanoic acid to give [6-(4-fluorophenoxy)-2-pyridyl]methyl 2-(N-formylamino)-3-methyl-butanoic acid, which is further reacted with methanol, yielding [6-4-fluorophenoxy)-2-pyridyl]methyl 2-amino-3-methylbutanoate.

EXAMPLE 8

A. To 2-(N-formylamino)-3-methylbutanoic acid (11.36 mmol) in THF:DMF (13 ml:5 ml) is added potassium carbonate (11.6 mmol) followed by α-cyano(6-phenoxy-2-pyridyl) mesylate (10.7 mmol) at RT, and the slurry is stirred for 48 hours. The slurry is then poured into ice-water, and the product is extracted with ether (3X). The ether layers are combined, washed with water until neutral and with brine, and dried over calcium sulfate. Filtration and evaporation of solvent give α-cyano(6-phenoxy-2-pyridyl)methyl 2-(N-formylamino)-3-methylbutanoic acid.

B. To 2.84 mmol of the ester from A above, in 3 ml methanol, is added 1N methanolic HCl (3 ml, 3.1 mmol), after which the solution is stirred for 19 hours. The solution is worked up as in Example 1(C) to give α-cyano(6-phenoxy-2-pyridyl)methyl 2-amino-3-methylbutanoate.

C. To α-cyano(6-phenoxy-2-pyridyl)methyl 2-amino-3-methylbutanoate (1.14 mmol) in 3 ml HMPA is added isopropyl iodide (5.8 mmol) followed by diisopropyl ethyl amine (2.23 mmol). The mixture is stirred at RT for 3 days. The reaction is poured into water and the product is extracted with ether (3X). The combined ether layers are washed with water and brine and dried over calcium sulfate. The solvent is evaporated and the product purified, yielding α-cyano(6-phenoxy-2-pyridyl)methyl 2-(N-isopropylamino)-3-methylbutanoate.

EXAMPLE 9

Following the procedure of Example 8, 3-chloro-2-buten-1-yl chloride is reacted with each of α-cyano(6-phenoxy-2-pyridyl)methyl 2-amino-3-methylbutanoate, α-methyl(6-phenoxy-2-pyridyl)methyl 2-amino-3-methylbutanoate and α-ethynyl(6-phenoxy-2-pyridyl)methyl 2-amino-3-methylbutanoate to yield α-cyano(6-phenoxy-2-pyridyl)methyl 2-[N-(3-chloro-2-butenyl)amino]-3-methylbutanoate
α-methyl(6-phenoxy-2-pyridyl)methyl 2-[N-(3-chloro-2-butenyl)amino]-3-methylbutanoate
and α-ethynyl(6-phenoxy-2-pyridyl)methyl 2-[N-(3-chloro-2-butenyl)amino]-3-methylbutanoate.

The α-methyl- and α-ethynyl(6-phenoxy-2-pyridyl)methyl esters of 2-amino-3-methylbutanoate are made as in Example 8.

EXAMPLE 10

A. To valine (17.1 mmol) in 20 ml HMPA is added isopropyl iodide (51.3 mmol) followed by potassium carbonate (34.2 mmol). The slurry is stirred at RT for 2 days, then poured into water and the product extracted with ether (3X). The combined ether layers are washed with water (until neutral) and with brine, and dried over calcium sulfate. Evaporation of the solvent gives isopropyl 2-(N-isopropylamino)-3-methylbutanoate. To 9.95 mmol of this product, in 20 ml methanol, is added sodium hydroxide (9.95 mmol) followed by 5 ml water. The solution is stirred at RT for 18 hours. The methanol-water is removed under vacuum; ether is then added to the residue and discarded, followed by addition of toluene (20 ml) which is then distilled off. The remaining solid is dried under high vacuum at 40°. This sodium salt of N-isopropyl valine (10 mmol) is placed in anhydrous methanol (5 ml) and 10 ml of 1 N methanolic HCl is added, with stirring. The mixture is filtered and the solvent is removed under vacuum to give N-isopropyl valine.

B. Finely ground N-isopropyl valine (31 mmol) in 150 ml dioxane is heated to 38°–40° and excess carbonyl chloride is slowly passed in over 4–5 hours. Dry air is then passed through the reaction for 18 hours, after which the dioxane is removed at 40° (20 mm) to yield 3,4-diisopropyl-oxazolidine-2,5-dione.

C. To 3,4-diisopropyloxazolidine-2,5-dione (5.4 mmol) and α-cyano(6-phenoxy-2-pyridyl)methanol (5.4 mmol), in 5 ml tetrahydrofuran, is added 4-dimethylaminopyridine (1.62 mmol), and the reaction is stirred at ambient temperature for 20 hours. The reaction is poured into water and the product is extracted with ether (3X). The combined ether layers are washed with water and with brine, dried over calcium sulfate, filtered and solvent evaporated to yield α-cyano(6-phenoxy-2-pyridyl)methyl 2-(N-isopropylamino)-3-methylbutanoate.

EXAMPLE 11

Following the procedure of Example 10, each of 3-(3-chloro-2-butenyl)-4-isopropyloxazolidine-2,5-dione, 3-(2-propynyl)-4-isopropyloxazolidine-2,5-dione, and 3-cyclohexyl-4-isopropyloxazolidine-2,5-dione is prepared and then reacted with α-cyano(6-phenoxy-2-pyridyl)methanol to give α-cyano(6-phenoxy-2-pyridyl)methyl 2-[N-(3-chloro-2-butenyl)amino]-3-methylbutanoate,
α-cyano(6-phenoxy-2-pyridyl)methyl 2-[N-(2-propynyl)amino]-3-methylbutanoate, and
α-cyano(6-phenoxy-2-pyridyl)methyl 2-(N-cyclohexylamino)-3-methylbutanoate.

The above three oxazolidines can also be reacted, using Example 10 methods, with α-methyl(6-phenoxy-2-pyridyl)methanol, yielding α-methyl(6-phenoxy-2-pyridyl)methyl 2-[N-(3-chloro-2-butenyl)amino]-3-methylbutanoate,
α-methyl(6-phenoxy-2-pyridyl)methyl 2-[N-(2-propynyl)amino]-3-methylbutanoate, and
α-methyl(6-phenoxy-2-pyridyl)methyl 2-(N-cyclohexylamino)-3-methylbutanoate.

EXAMPLE 12

To a mixture of 2-(N-formylamino)-3-methylbutanoic acid (1.49 mmol) and 4-N,N-dimethylaminopyridine (0.186 mmol) in 20 ml dichloromethane is added (6-phenoxy-2-pyridyl)methylthiol (1.24 mmol) under nitrogen. The mixture is cooled in an ice bath and dicyclohexylcarbodiimide (1.49 mmol) is added, after which the mixture is allowed to warm to RT and stirred for 18 hours. It is then filtered and brought up in ether, washed with water (2X) and with brine, dried over calcium sulfate, stripped, purified by filtration and stripped again to yield S-(6-phenoxy-2-pyridyl)methyl thiolester of 2-(N-formylamino)-3-methylbutanoic acid. Following the procedure of Example 1(c), the thiolester is reacted with 1 N methanolic HCl, in anhydrous methanol, giving S-(6-phenoxy-2-pyridyl)methyl thiolester of 2-amino-3-methylbutanoic acid.

The thiol, (6-phenoxy-2-pyridyl)methylthiol, is prepared by the reaction of (6-phenoxy-2-pyridyl)methyl bromide with thioacetic acid using sodium hydride to form the thio ester which is then converted to the desired thiol using lithium aluminum hydride.

Following the procedure of Example 3, the p-toluenesulfonic acid salt of the S-(6-phenoxy-2-pyridyl)methyl thiolester of 2-amino-3-methylbutanoic acid is reacted with 3-chloro-2-buten-1-yl chloride to give S-(6-phenoxy-2-pyridyl)methyl thiolester of 2-[N-(3-chloro-2-butenyl)amino]-3-methylbutanoate.

EXAMPLE 13

Using the method of Example 2, (6-benzoyl-2-pyridyl)methyl 2-amino-3-methylbutanoate is reacted with each of 2-chloro-2-propen-1-yl bromide and 3- chloro-2-buten-1-yl chloride to yield (6-benzoyl-2-pyridyl)methyl 2-[N-(2-chloro-2-propenyl)amino]-3-methylbutanoate and (6-benzoyl-2-pyridyl)methyl 2-[N-(3-chloro-2-butenyl)amino]-3-methylbutanoate.

The compound (6-benzoyl-2-pyridyl)methyl 2-amino-3-methylbutanoate is made from the reaction of (6-benzoyl-2-pyridyl)methyl bromide and 2-(N-formylamino)-3-methylbutanoic acid, following the procedures of Example 1.

What is claimed is:

1. A compound of the formula (IV'):

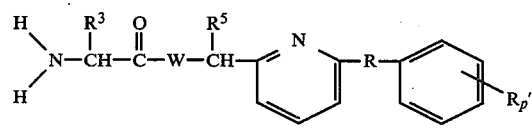

wherein,
W is oxygen or sulfur;
p is zero, one or two;
R is oxygen, sulfur, methylene or carbonyl;
$R^3$ is lower alkyl of 2 to 5 carbon atoms, lower alkenyl of 2 to 5 carbon atoms or lower cycloalkyl of 3 to 4 carbon atoms;
$R^5$ is hydrogen, cyano, methyl, ethyl, ethynyl or Trifluoromethyl; and
R' is fluoro, bromo, chloro, trifluoromethyl, methyl, methoxy or methylthio.

2. A compound according to claim 1 wherein $R^3$ is isopropyl.

3. A compound according to claim 2 wherein W is oxygen and R is oxygen.

4. A compound according to claim 3 wherein $R^5$ is hydrogen, cyano or methyl.

5. A compound according to claim 4 wherein p is zero or one and R' is fluoro.

* * * * *